United States Patent [19]
Murray et al.

[11] Patent Number: 5,240,164
[45] Date of Patent: Aug. 31, 1993

[54] ROTATING HEAD SKIN STAPLER

[75] Inventors: Michael A. Murray, Bellevue, Ky.; John F. Love, Cincinnati, Ohio; James D. Hughett, Cincinnati, Ohio; Randy R. Stephens, Fairfield, Ohio; Richard F. Schwemberger, Cincinnati, Ohio

[73] Assignee: Ethicon, Inc., Somerville, N.J.

[21] Appl. No.: 931,814

[22] Filed: Aug. 18, 1992

Related U.S. Application Data

[60] Division of Ser. No. 806,951, Dec. 12, 1991, Pat. No. 5,161,725, which is a continuation of Ser. No. 479,318, Feb. 13, 1990, abandoned.

[51] Int. Cl.⁵ .......................................... A61B 17/068
[52] U.S. Cl. .................................. 227/175; 227/177; 227/19
[58] Field of Search ................. 227/19, 175, 176, 177, 227/182

[56] References Cited

U.S. PATENT DOCUMENTS

| | | | |
|---|---|---|---|
| 2,086,922 | 7/1937 | Peterson | 1/49 |
| 4,204,623 | 5/1980 | Green | 227/19 |
| 4,391,402 | 7/1983 | Campbell et al. | 227/121 |
| 4,458,835 | 7/1984 | Li et al. | 227/121 |
| 4,489,875 | 12/1984 | Crawford et al. | 227/19 |
| 4,519,532 | 5/1985 | Foslien | 227/8 |
| 4,592,498 | 6/1986 | Braun et al. | 227/19 |
| 4,596,350 | 6/1986 | Smith et al. | 227/19 |
| 4,618,086 | 10/1986 | Li et al. | 227/19 |
| 4,648,542 | 3/1987 | Fox et al. | 227/19 |
| 4,691,853 | 9/1987 | Storace | 227/19 |
| 4,796,793 | 1/1989 | Smith et al. | 227/19 |
| 4,811,886 | 3/1989 | Murray | 227/19 |
| 4,951,860 | 8/1990 | Peters et al. | 227/177 |

*Primary Examiner*—Frank T. Yost
*Assistant Examiner*—Rinaldi Rada
*Attorney, Agent, or Firm*—Paul A. Coletti

[57] ABSTRACT

A surgical stapler having a trigger attached to a ratcheting mechanism for preventing the refiring of the stapler trigger with a staple loaded within a forming mechanism. In addition, the mechanism contains driver buffering means to prevent the sharp reduction in opposing force driving formation of a staple. The staples are constantly maintained in proper orientation during transfer from a track to the forming site, and are self-centering on the former, and have an oversized crown so that cold-worked areas on each staple do not hinder forming.

3 Claims, 10 Drawing Sheets

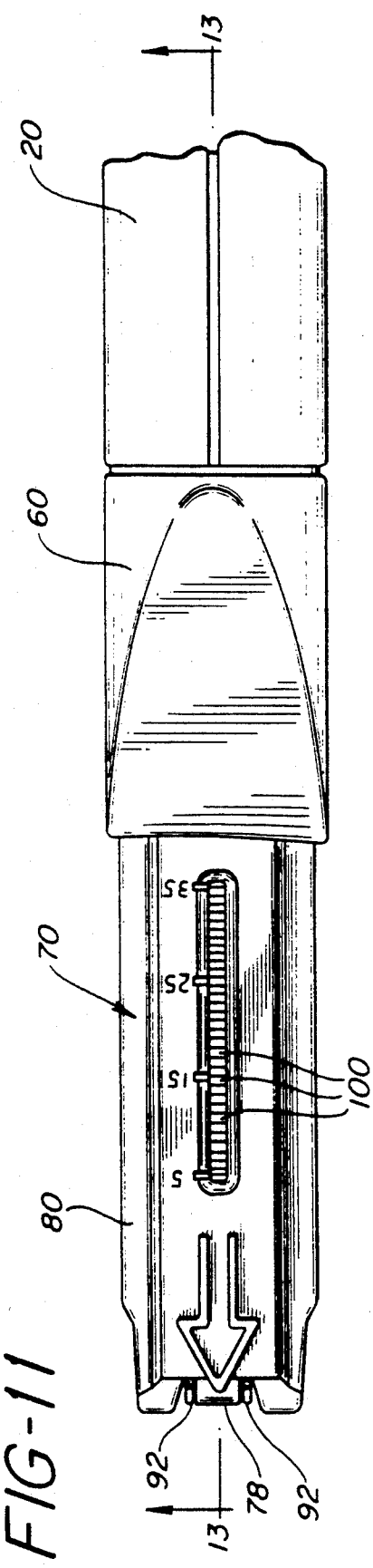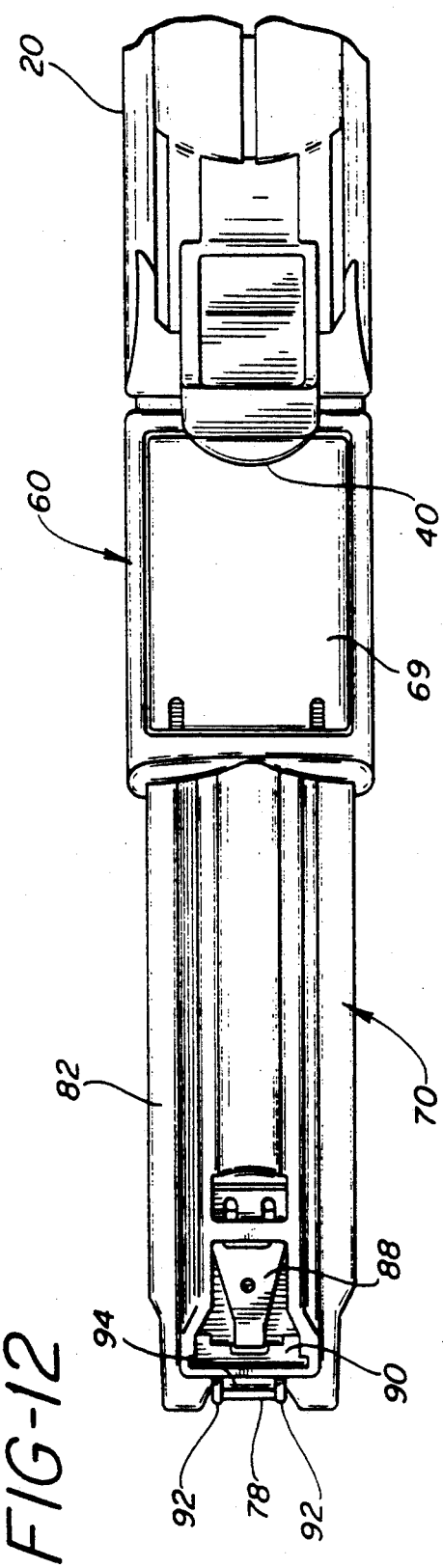

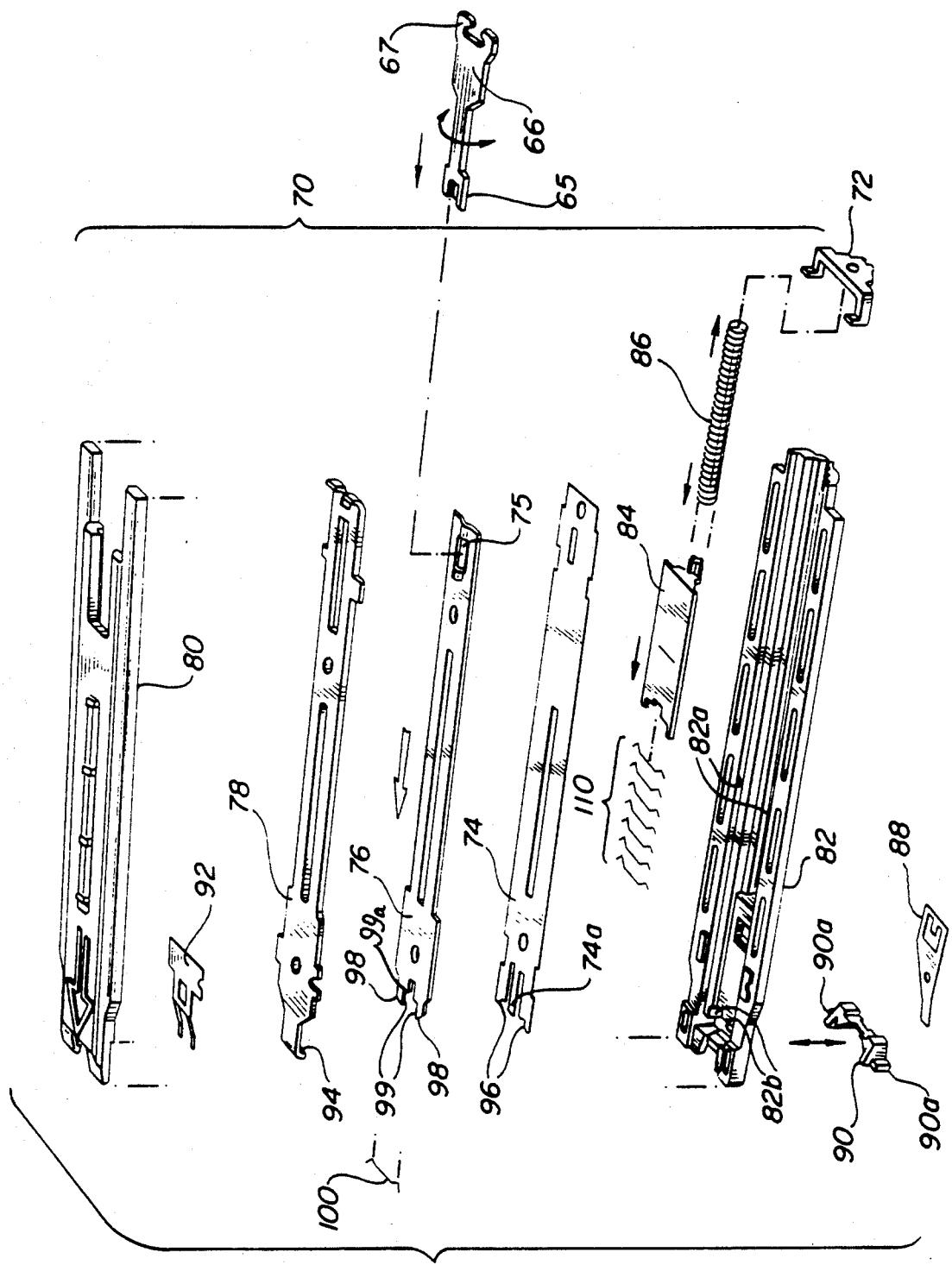

ROTATING HEAD SKIN STAPLER

This is a division, of application Ser. No. 806,951, filed Dec. 12, 1991, now U.S. Pat. No. 5,161,725, which is a continuation of application Ser. No. 479,318, filed Feb. 13, 1990, abandoned, both of which are hereby incorporated by reference.

FIELD OF THE INVENTION

The invention relates generally to surgical staplers. More specifically, the invention relates to skin staplers used during surgery Most specifically, the invention relates to surgical skin staplers having rotating heads.

BACKGROUND OF THE INVENTION

In recent years, the use of skin staplers has become one of the preferred methods of wound closure. Skin staplers rapidly and accurately close surgical wounds. Effective tissue eversion during skin stapling allows for rapid healing, and reduces the possibility of infection.

Nonetheless, as skin staplers have improved, so has the need for increased reliability and various new and unforeseen characteristics. Thus, it is greatly desirable to provide skin staplers which contain reliable staple feeding mechanisms. Previous staple feeding mechanisms have either been bulky or complex, or even quite unreliable. In order to form a more accurate skin stapler, the need exists for a reliable feeding mechanism able to fit within a staple cartridge or track, and demonstrate a thin profile in order to provide accurate, yet visible staple placement onto a surgical site.

In addition, previous systems have contained unreliable drive mechanisms. Previous systems must proceed completely along a single stroke to be fired. Not completely firing this type of stapler has previously increased the likelihood of jamming, causing delay and unreliability in the system. Of course, even if one disregards the possibility of the stapler jamming, if no provision is made for stopping the firing sequence, it is possible to lose accurate control and placement of the surgical staple.

In many staplers, feel of the mechanism is quite important. If the surgeon is able to "feel" a staple as it is being driven into the skin, the surgeon can properly place the staples and close the wound. Extremely important to such "feel" is the completion of the driving stroke. Inadvertently, the triggering mechanism goes through a rapid change in the force encountered at the stapling site. This may cause the trigger mechanism to "jump" in the surgeon's hand, due to recoil from these forces. This affects the feel to the surgeon, who desires a very smooth stroke in the stapler.

In addition, the track in which the staples are formed has been very difficult to control in manufacturing processes. This is due, in part, to the very tight manufacturing tolerances through which the staple and cartridge must be held to prevent malforming of the staple. In some staplers, especially those where the preformed staple is larger in width than its final formed shape, it is difficult to control the formation of the staple while allowing for accurate placement. Thus, it is desirable to provide a system where the staple itself enhances its own accurate placement at the forming site and, ultimately, in closing the wound.

Finally, when forming the staple, what is most necessary is repeatably creating a properly shaped staple. This allows the surgeon to position and properly place the staple on the skin. This creates the proper environment on the skin for quick and safe wound healing.

Furthermore, these desirable features of a skin stapler should be incorporated into a skin stapler with a rotating head. The rotating head concept allows the user to place the staple at the wound site, and then to examine the site before closure, without raising the stapler from the surface of the skin. In this way, the user is able to maintain contact throughout closure.

SUMMARY OF THE INVENTION

Accordingly, it is an object of the invention to provide a skin stapler with a rotating head where the staples are reliably transferred from the cartridge track in which the staples are maintained to the staple forming site.

It is another object of the invention to provide a stapler where the user can relax the grip on the stapler driving mechanism without potentially harming the formation of the staple, or jamming the staples in the staple forming track.

It is yet another object of the invention to provide a smooth and accurate placement and closure of the staple without "snap" felt in the trigger mechanism.

It is still another object of the invention to allow ease of manufacture while ensuring accurate placement and positioning of staples on the staple former and in the skin.

It is yet another object of the invention to center the staples on an anvil surface prior to and during staple forming to achieve a consistently more precise formed skin staple.

It is finally an object of the invention to incorporate all of these characteristics into a stapler containing a rotating staple head, whereby staple forming precision, reliable ease of function, and accuracy are embodied in a stapler having many versatile wound closure capabilities.

These and other objects of the invention are accomplished in a surgical stapler with a rotating head where the staple transfer mechanism contains a lifter spring which provides the force necessary to lift the staple across the stapler head from a feeding track into a parallel staple forming track. This lifter mechanism supports the staple crown and legs to properly maintain the staple in position before the forming stroke. The lifter mechanism also contains a tab which maintains the staple position on the staple lifter until the staple is moved to the staple forming track.

At the opposite end of the stapler, the driving mechanism contains a ratcheting means which allows the user to relax the stroke during forming, and yet prevent jamming. A buffer mechanism provides a resistive force to the driver mechanism, thus spreading staple forming forces and minimizing any "snap" during the final stages of staple forming.

Finally, the stapler has a wing-shaped forming mechanism which closely parallels the winged shape profile of the staples. This former mechanism centers the staple on the anvil and ensures reliable and consistent staple formation and placement on the skin. A reduced anvil size causes the staple to maintain an accurate and Precise shape during forming.

These objects of the invention will be better understood by the following Detailed Description of the Drawings taken in conjunction with the Detailed Description of the Invention.

DETAILED DESCRIPTION OF THE DRAWINGS

FIG. 11 is a partial top plan view of the rotating head skin stapler;

FIG. 12 is a partial bottom plan view of the rotating head skin stapler;

FIG. 19 is an exploded perspective view of the staple cartridge of this invention.

DETAILED DESCRIPTION OF THE INVENTION

Figure 1:
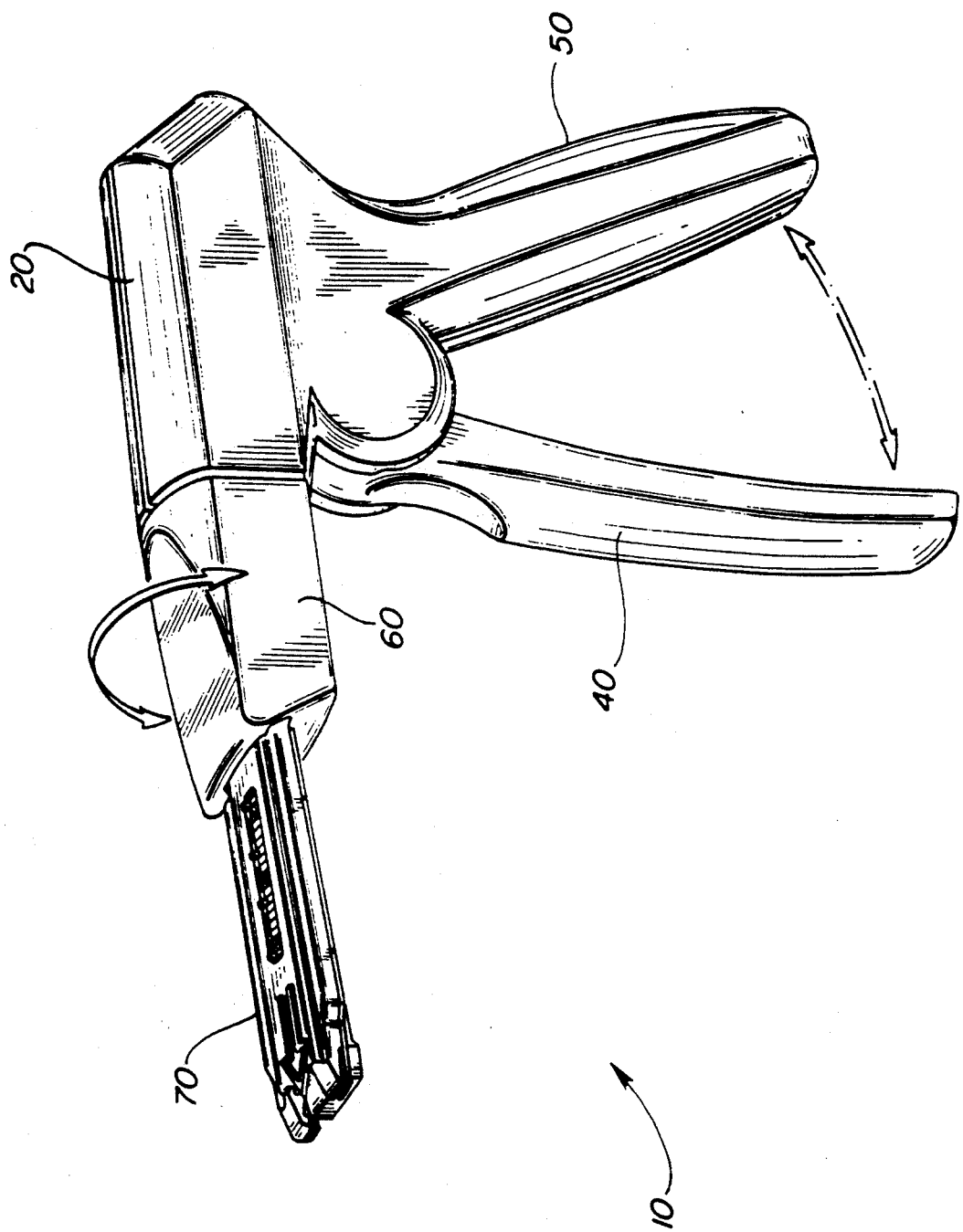
FIG. 1 is a perspective view of the rotating head skin stapler of this invention.
Figure 2:
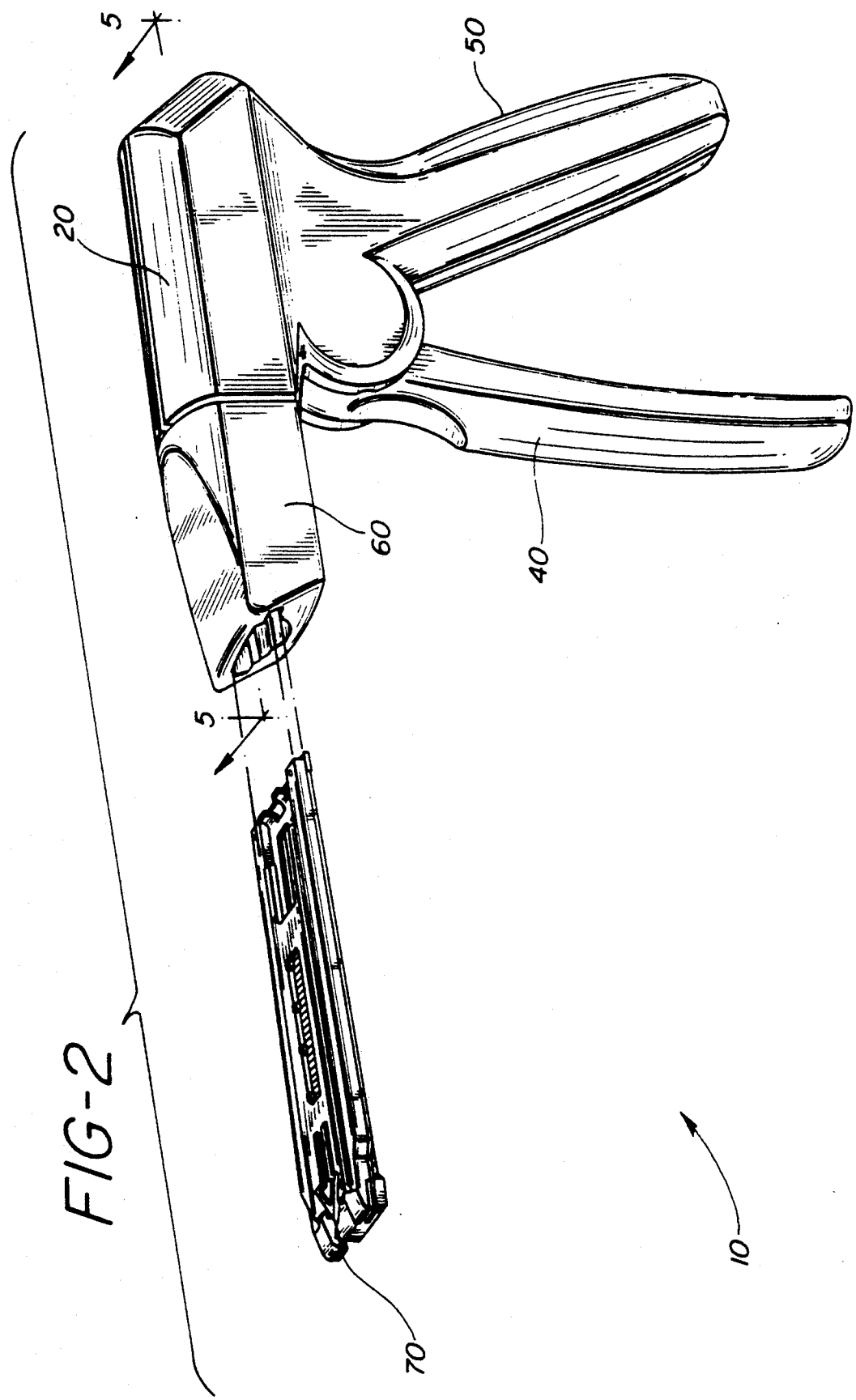
FIG. 2 is an exploded perspective view showing the replaceable staple cartridge removed from the rotating head.
Figure 3:
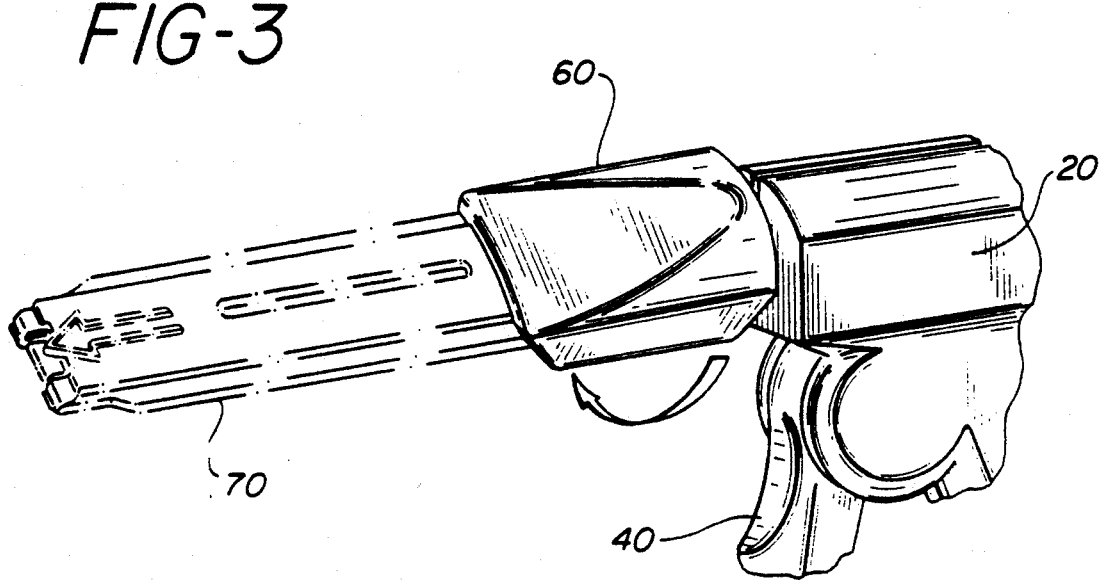
FIG. 3 is a partial perspective view showing the rotating head in one possible orientation.
Figure 4:
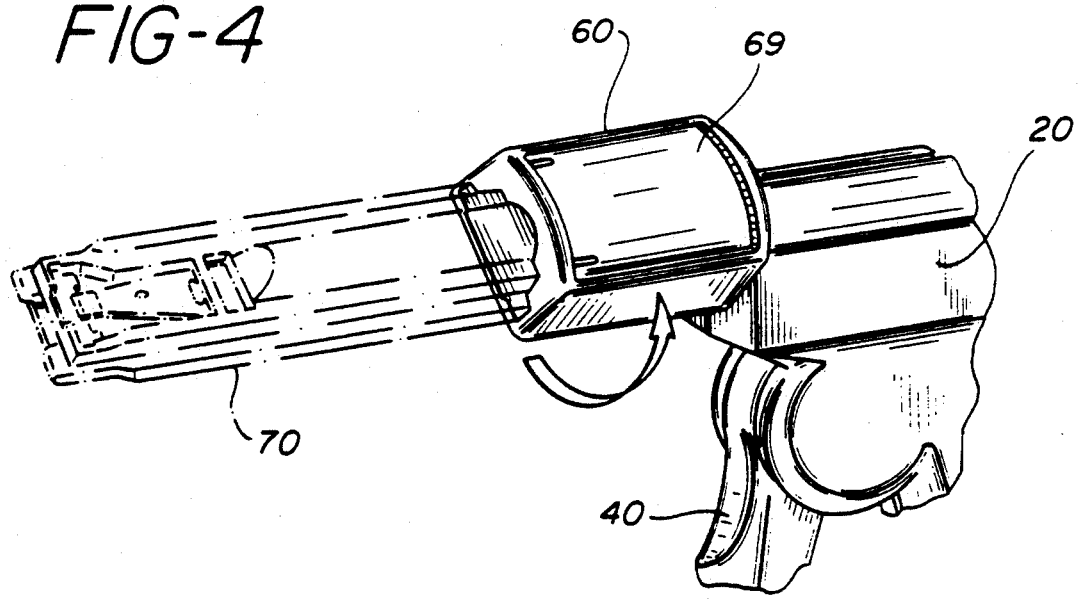
FIG. 4 is a partial perspective view of the rotating head in another possible orientation.

As seen in FIGS. 1 through 4, the rotating head skin stapler 10 contains a base 20 housing a drive mechanism which is activated by a trigger 40 squeezed within handle 50. The drive mechanism contained in the base 20 causes staples to be fired from cartridge 70. The rotating head 60 allows orientation of the cartridge 70 in any angular direction in relation to base 20 on the wound surface to be closed, as best seen in FIGS. 3 and 4.

Various aspects of the rotating head skin stapler 10 will now be explained Intrinsic to the rotating head skin stapler 10 is rotating head 60. This rotating head 60 is attached to the base 20 by means of collar 64 enmeshed within holding cylinder 21 as better seen in FIGS. 5 and 6. Drive train 66 is rotatably connected at its proximal end to drive block 44 and at its distal end contacts former 76 within the plane of cartridge 70. Drive train 66 fits axially into collar 64 on rotating head 60. Drive train 66 is generally flat in shape, and constantly enmeshed between cartridge 70 and rotating head 60, as will be explained later. Because drive train 66 and cartridge 70 are fitted into the center of rotating head 60, and rotate about drive block 44, during rotation they maintain positional relationship with base 20, so that the orientation of cartridge 70 is optional to the user. For instance, as seen in FIG. 4, cartridge 70 has been rotated to expose head plate 69.

Figure 5:
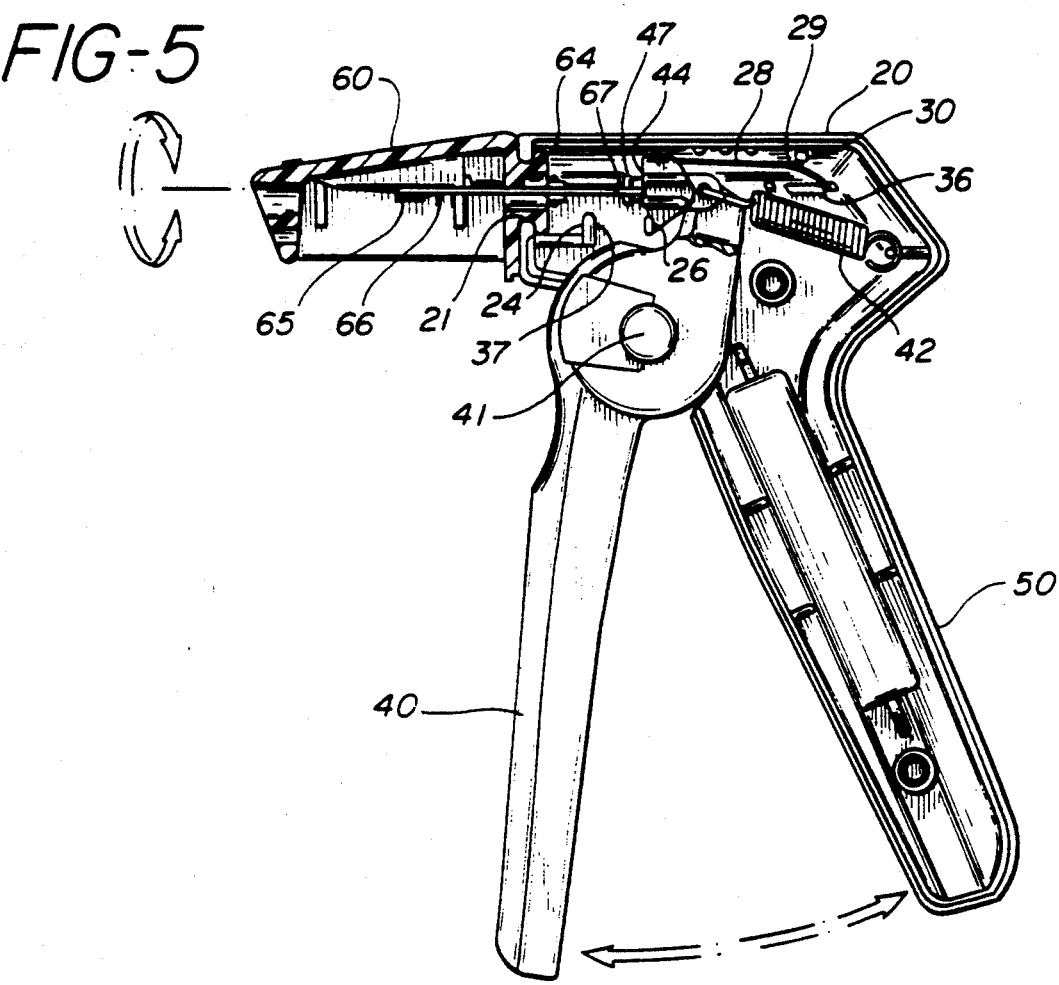
FIG. 5 is a cross-sectional view taken along line 5—5 of FIG. 2.
Figure 6:
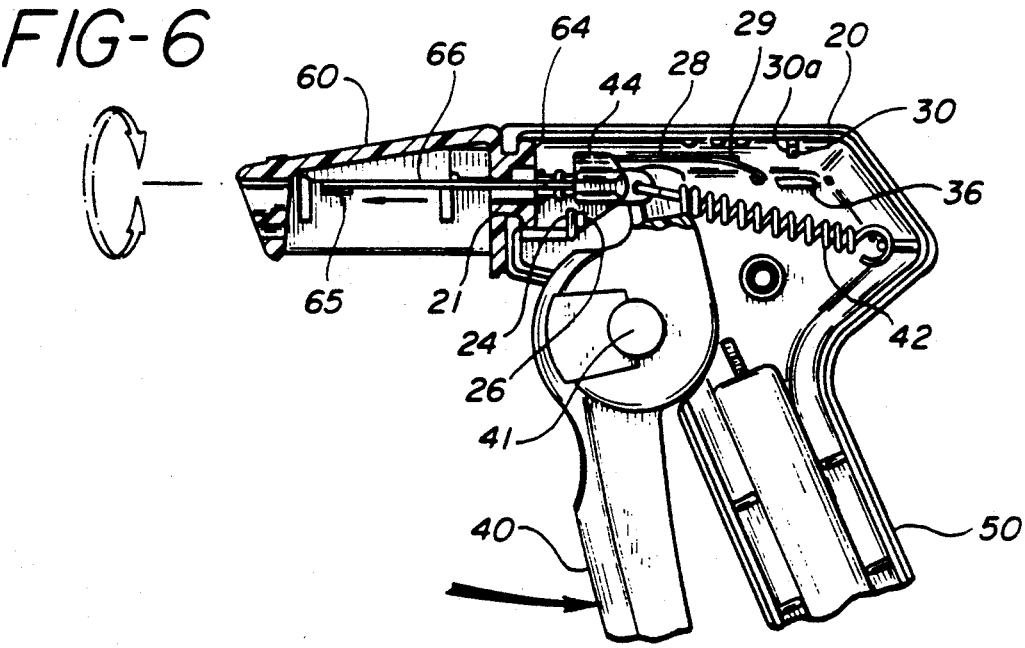
FIG. 6 is a view similar to FIG. 5 after compressing the handle and trigger.

At its proximal end, drive train 66 is rotatably engaged with drive block 44. This is accomplished by inserting notched perforations 67 at the proximal end of drive train 66 around circular node 47 of drive block 44, as better seen in FIGS. 9 and 10. Thus, the notched perforations 67 are free to rotate about circular node 47 to allow drive train 66 to rotate about drive block 44, as seen in FIGS. 5 and 6. In this way, wherever rotating head 60 is oriented with drive train 66 contained therein, drive train 66 remains attached to drive block 44, and transfers force through the rotating head 60 and cartridge 70 combination.

For operation of the stapler, it is necessary for drive train 66 to have force imparted on it by drive link or drive block 44. As drive train 66 is rotatably attached by notched perforations 67 onto the drive block circular node 47, only force exerted along the same axis as drive train 66 will be imparted from drive block 44.

As better seen in the enlarged and various views of the interior of base 20 in FIGS. 5, 6, 7, 8, 9 and 10, drive block 44 is maintained on travel axis 46 through use of guide channels 48. When drive block 44 is moved linearly along guide channels 48, the wings 49 on drive block 44 are maintained about guide channels 48. Thus, drive block 44 is ensured of travel along travel axis 46. Trigger 40 contacts drive block 44, and therefore imparts force on drive block 44 along travel axis 46.

Figure 7:
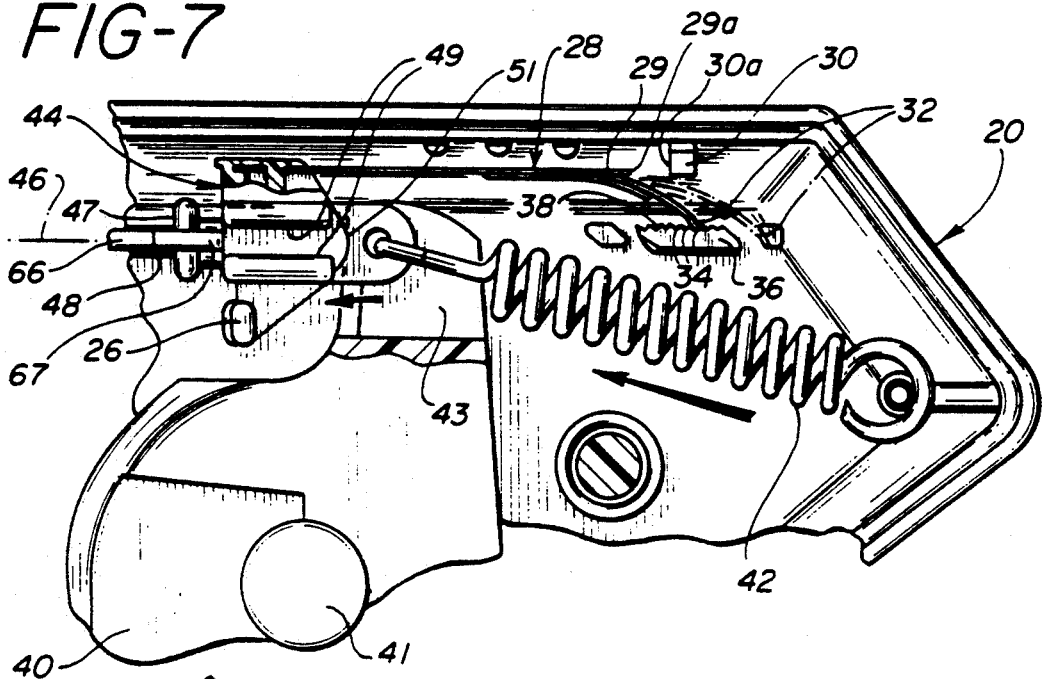
FIG. 7 is a fragmentary view in cross-section of the trigger mechanism of the invention.

Trigger 40 rotates about pivot 41 within handle 50. As seen in FIG. 7, elongated trigger projections 43 contact rear surface 51 of drive block 44. Rotation of the trigger 40 about pivot 41 necessarily causes the user to impart forces on drive block 44 along travel axis 46. This, in turn, causes motion of drive block 44 along travel axis 46, and operation of the stapling mechanism in cartridge 70.

Figure 9:
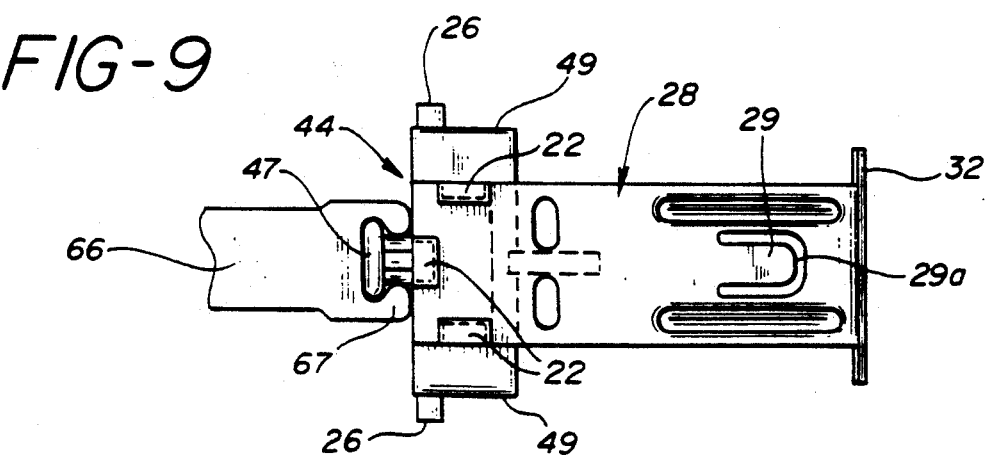
FIG. 9 is a plan view of the drive block and drive train rotating mechanism.
Figure 10:
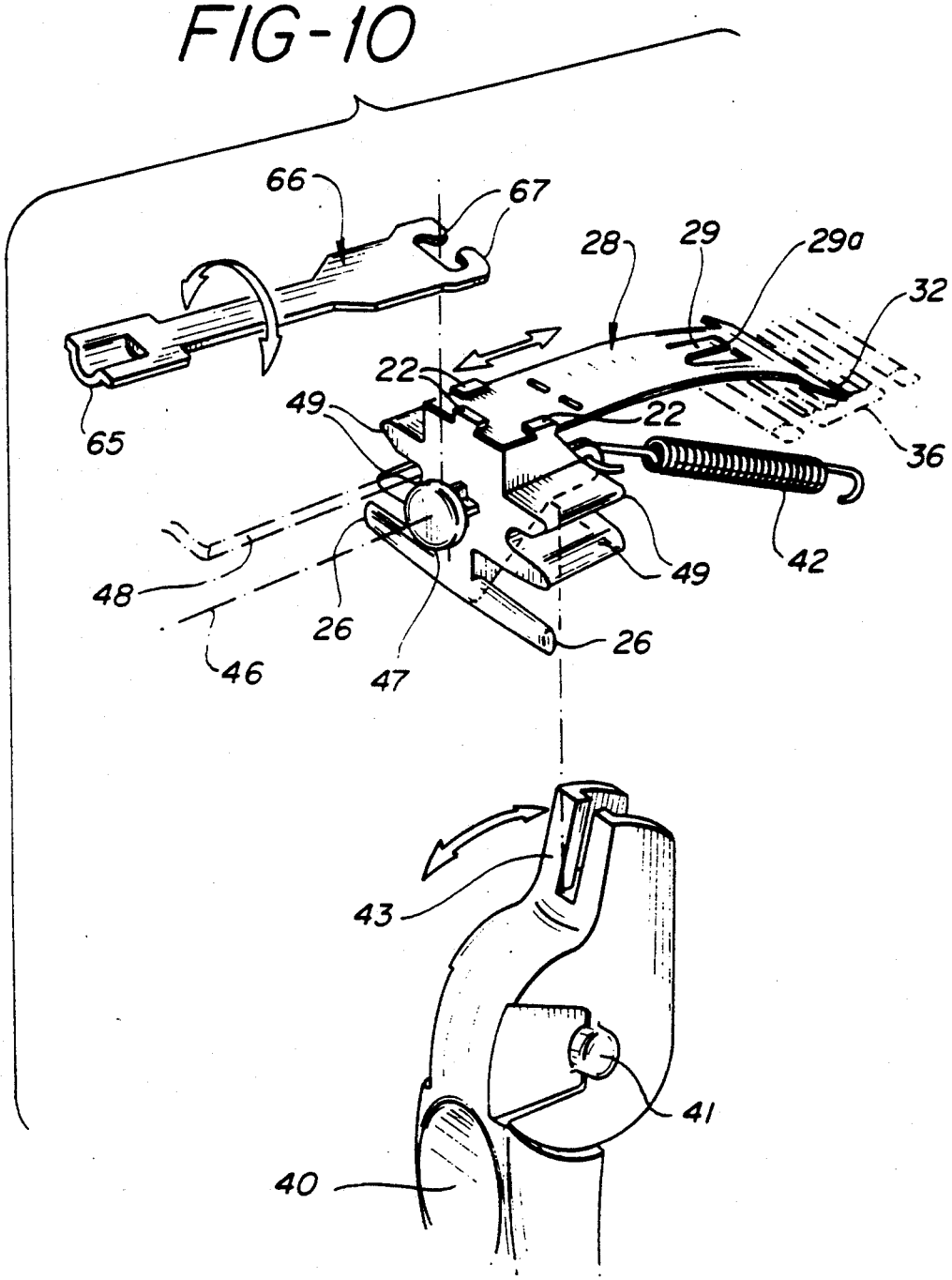
FIG. 10 is a perspective view of the drive block and drive train mechanism.
Figure 13:
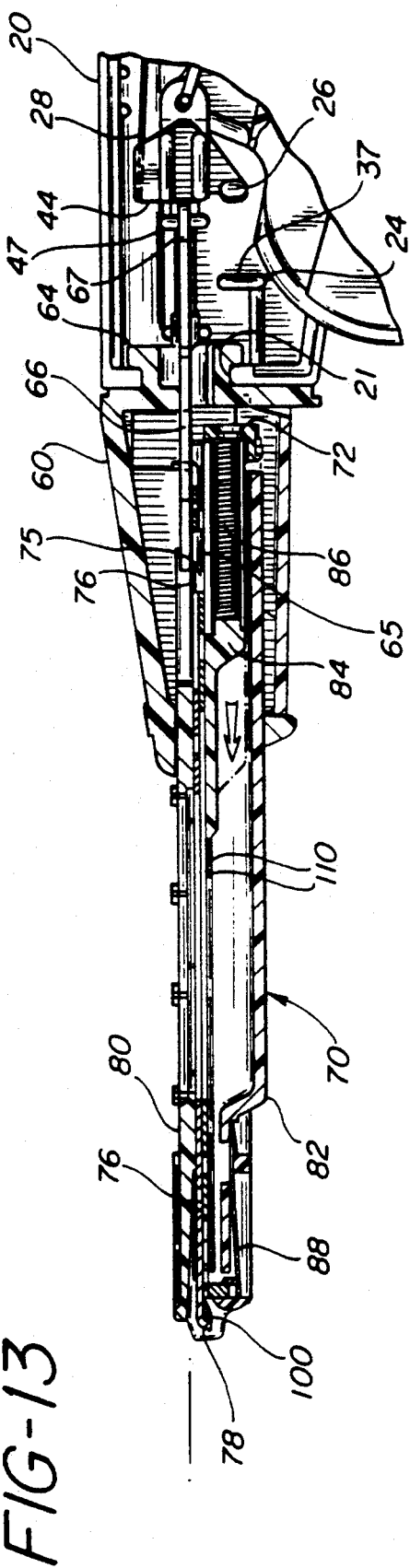
FIG. 13 is a cross-sectional view taken along line 13—13 of FIG. 11.
Figure 14:
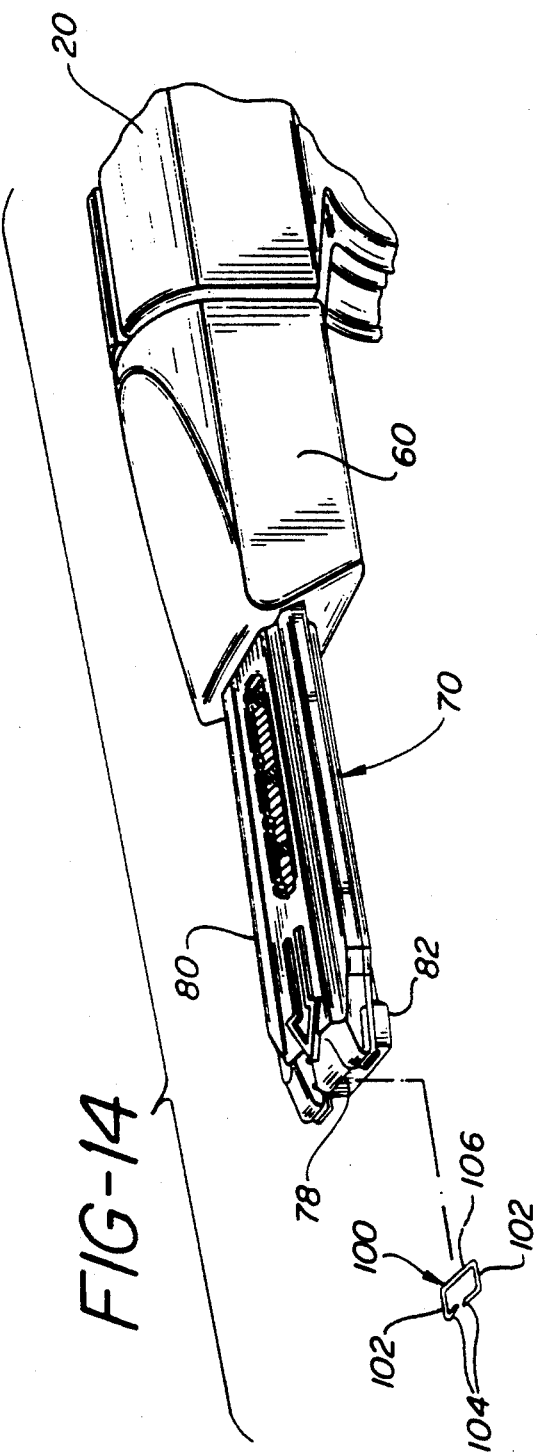
FIG. 14 is a partial perspective view showing a formed staple which released from the distal end of the staple cartridge.

Improvements to the rotating head skin stapler 10 are seen in the driving mechanism employed in use of trigger 40. Drive block 44 has attached to it the pawl 28, by means of tabs 22 folded over the pawl 28, as seen in FIGS. 9 and 10. When trigger 40 is cocked by rotation about pivot 41, drive block 44 causes pawl 28 to move linearly in unison with drive block 44 along axis 46. The rear of drive pawl 28 encounters surface 30a on engagement block 30 at surface 29a on engagement tab 29, as seen especially at FIGS. 5 and 7 in a position normal to travel axis 46. Engagement tab surface 29a becomes enmeshed with engagement block surface 30a to prevent rearward linear motion of drive block 44 along travel axis 46 by holding pawl 28 in teeth 38.

Relying further on FIGS. 6, 7 and 10, upon further motion of the trigger 40, the stopping surface 32 of drive pawl 28 contacts multi-tooth rack 36 on edges 34 of teeth 38. Stopping surface 32 is normal to travel axis 46 and continues to prevent motion of drive block 44 into base 20 in incremental steps throughout the remainder of the stroke of trigger 40. Such continuous maintenance of the position of drive block 44 affirmatively prevents jamming of the stapler 10, by preventing drive block 44 and consequently trigger 40 from retracting linearly along travel axis 46 or recocking during a single stroke of trigger 40. The stapling mechanism in cartridge 70 will not reload, and therefore two staples will not be processed simultaneously at the forming site.

Accordingly, during motion of drive pawl 28 along multi-tooth rack 36, each of the teeth 38 hold drive pawl 28 at stopping surfaces 32 on edges 34 until full rotation of the trigger 40 is accomplished. Then, the pawl 28 acts like a leaf spring and recoils so that the surface of pawl 28 clears the lower surface of multi-tooth rack 36. This occurs because tab 29a is no longer constrained by block surface 30a, so that pawl 28 now moves upward out of engagement with rack 36. This allows drive spring pawl 28 to return to its original position. Return spring 42 causes trigger 40 to return drive block 44 along travel axis 46 after one full stroke of trigger 40.

As further seen in the enlarged view of drive block 44 as in FIG. 10, there are contained on block 44 winged-shaped buffers 26. These wing-shaped buffers 26 provide resistive force encountered by the user during the forward linear motion of drive block 44, near completion of the stroke of the trigger 40. Ordinarily, at the completion of a firing stroke, staples 100 have been formed, but the user continues to drive trigger 40. In order to reduce any "snap" in the feel of the trigger 40, due to the continued force of former 76 against staple crown 106 of the (now formed) staple 100, it is necessary to minimize forward linear motion of drive block 44 and spread the force over a larger surface area by imparting a resistive force opposite the direction of motion of drive block 44, and thus reduce the pressure exerted on drive block 44.

Figure 8:
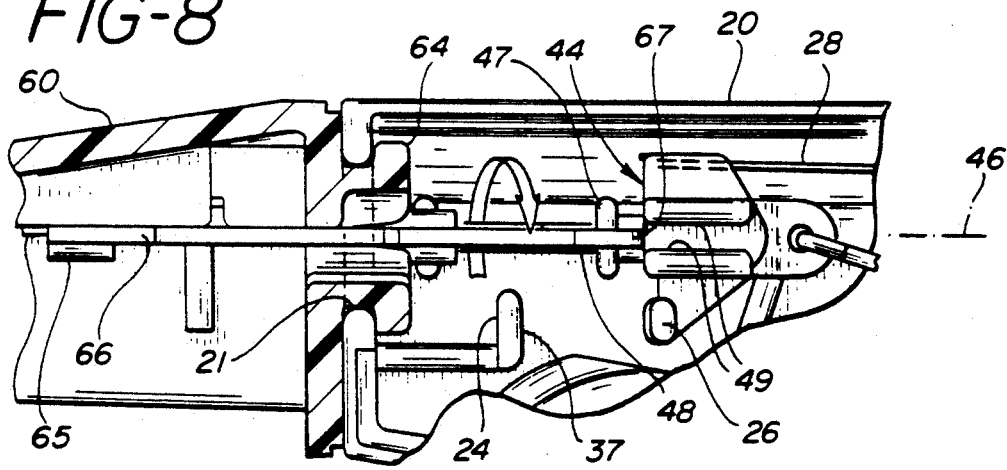
FIG. 8 is a fragmentary view of the buffer mechanism.

As seen in FIGS. 5, 6 and 8, block-shaped stops 24 are provided in base 20 which engage the buffers 26 near the end of the stroke of trigger 40. These stops 24 contain stopping surfaces 37 which cause the buffers 26 to elastically bend near the end of the stroke of trigger 40. In this way, the force actually imparted by the trigger 40 reduced by spreading forces over a larger surface area near the end of the stroke, and the user experiences no "snap" caused by impact of former 76 on staple 100 after complete staple forming.

In summary, the trigger anti-jamming mechanism and the drive link buffer of the invention accomplish the following steps: The multi-tooth rack 36 provides engagement surfaces 34 on the teeth 38 which are normal to the travel axis 46 and therefore provide a resistive force parallel to the travel axis 46. The drive pawl 28, made of a resilient material to resist permanent deformation, engages the multi-tooth rack 36 in a direction normal to motion of drive block 44 to provide resistive forces parallel to travel axis 46. The engagement tab surface 29a on spring pawl 28 provides early engagement with block engagement surface 30a in order to prevent misfiring of the stapling mechanism in cartridge 70 at an earlier position of trigger 40 stroke. The engagement of the pawl 28 with the rack 36 allows the user to have a smoother feel of the surgical stapling instrument throughout the stroke of trigger 40.

In addition, with the buffers 26 molded as an integral part of the drive block 44, as the stroke of the former 76 approaches the final stage of contact between staple crown 106 and anvil forming surface 94 (as later explained), buffers 26 contact stopping surfaces 32. Because buffers 26 are elastic, they begin to bend and resist any continuing force imparted by drive block 44. In this way, forward motion of the block 44 is slowed and greatly reduces the impact of former 76 against the staple crown 106. This results in a more consistent force to form the staples, and avoids any snap felt by the user during trigger 40 stroke.

Figure 17:
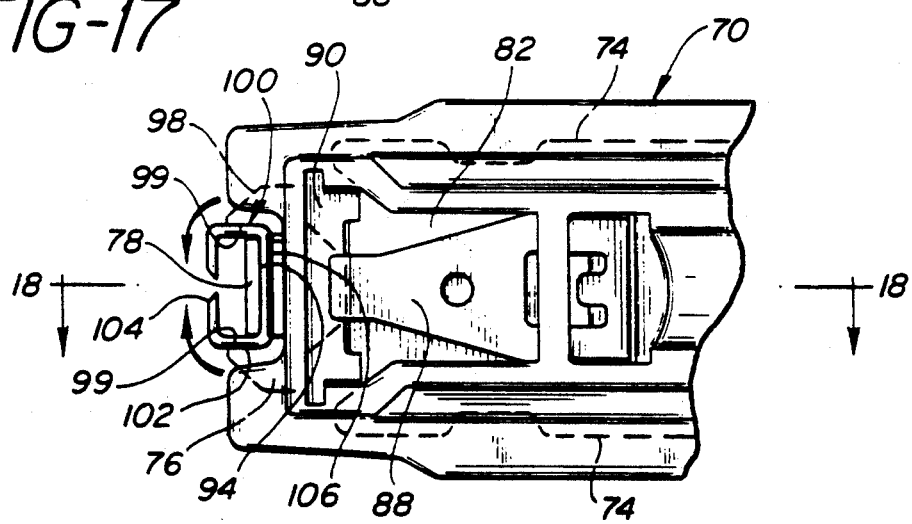
FIG. 17 is a partial bottom plan view of the staple cartridge just after forming the staple.
Figure 18:
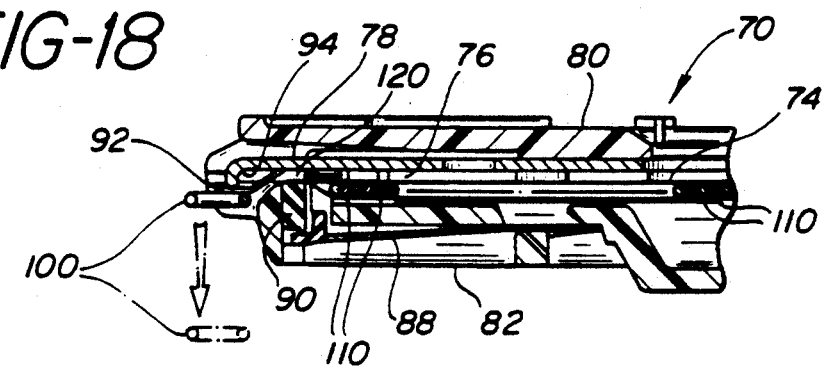
FIG. 18 is a cross-sectional view taken along line 18—18 of FIG. 17.

Other aspects of the invention are seen in the staple cartridge 70. Specifically, as seen in FIGS. 17 through 19 drive train 66 is connected to former 76 in the cartridge 70 by sliding plate 65 into gripping receiver 75a. Former 76 contacts the first of a group of staples 100 at the head of staple stack 110. These staples 100 contain wings 102, legs 104, and crown 106. Lifter 90 holds a staple 100 in place and maintains staple 100 in position due to forced imparted by spring 88 on lifter 90, as later explained. During formation of a staple 100, crown 106 contacts the forming surface 94 of anvil 78 at a forming site removed from staple stack 110. This is better explained in U.S. Pat. No. 4,811,886, assigned to the common assignee as this invention, and incorporated herein by reference.

Figure 15:
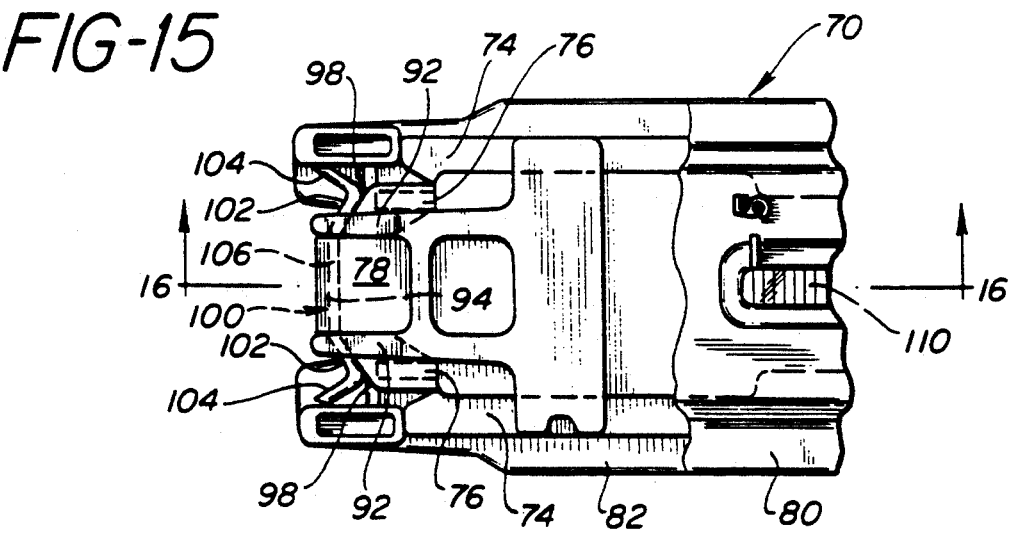
FIG. 15 is a partial top plan view of the distal portion of the staple cartridge with the top of the cartridge partially broken away for clarity.
Figure 16:
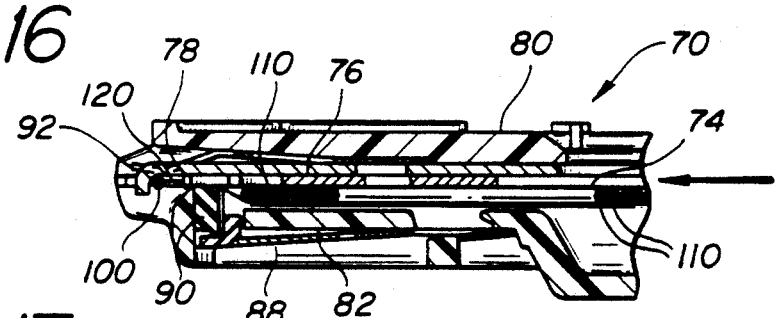
FIG. 16 is a cross-sectional view taken along line 16—16 of FIG. 15.

As seen in the views of the former 76 in FIGS. 15 and 19, former edges 98 are angled like the gull wing shaped wings 102 and legs 104 of staple 100. The former extends proximally from the rectangular inner profile 99a located between shoulders 99. With the improved former edges 98, the legs 104 become self-centering within staple forming track 120, and force is kept on the inside edges of the staple legs 104 during forming. In so doing, the staple 100 stays centered on former 76 until staple 100 is formed around anvil forming surface 94. Alignment between former 76 and anvil 78 thus becomes the controlling alignment criterion, rather than relying on tolerances of staple 100. If the staple 100 is positioned slightly to one side of the anvil forming surface 94, the funnelling effect of the former edges 98 biases or "pulls" the staple 100 to the center within shoulders 99 and controls it throughout forming of the staple 100. The continuous force imparted on the inside of staple legs 104 during the firing stroke decreases the possibility of malformation of the staple during forming, as seen in FIGS. 15 through 18.

In addition, as seen in FIGS. 15 and 17, anvil forming surface 94 on anvil 78 in the cartridge 70 is smaller in width than staple crown 106. In this way, crown 106 is shaped entirely around anvil forming surface 94. Because the crown 106 is wider than anvil forming surface 94, the cold worked areas of the staple found at the unions of crown 106 and wings 102 are shaped in spaced-apart relationship to the forming surface 94. Thus, the cold worked areas of the staple 100 are avoided during forming about forming surface 94, reducing forces necessary to form a staple 100.

Another improvement is seen in the lifter mechanism in cartridge 70 of the stapler. Lifter 90 is controlled by lifter spring 88 on the lower staple housing 82 of staple cartridge 70. Lifter spring 88 causes lifter 90 to move one staple 100 from the stack of staples 110 in staple feeding track 82a of the lower staple housing 82 of the cartridge 70. The staples in stack 110 are moved along feeding track 82a by feeder shoe 84, which is urged distally by feeder spring 86. Lifter spring 88 causes lifter 90 to lift a staple 100 across profile 96 in intermediate staple housing 74, which defines a vertical passage between parallel feeding track 82a and forming track 120.

The profile 96 on intermediate staple housing 74 has a shape corresponding to the staples 100 maintains the staple 100 on lifter 90 properly within tab 74a of intermediate housing 74. Lifter 90 therefore prevents transfer and double loading of staples from the stack of staples in feeding track 82a onto the staple forming stack 120.

Retainer cap 72 holds together upper staple housing 80 and lower staple housing 82 and maintains feeder spring 86 in cartridge 70 so that the force urging staple stack 110 along feeder track 82a and into a staple forming track 120 is uninterrupted. Staple kick-off spring 92 causes the formed staples 100 to be kicked off from the anvil forming surface 94 when formed and placed in the skin and former 76 is retracted. Top staple housing 80 of cartridge 70 comprises the upper surface of forming track 120.

The staple transfer mechanism found in lifter 90 lifts the staple between the parallel staple stack 110 in staple feeding track 82a and staple forming track 120 incorporated in cartridge 70. The single staple 100 is supported along its crown 106 and legs 104 by the lifter 90 during lifting from the staple feeding track 82a to staple forming position in staple forming track 120. Tab 75 located on the distal end of the intermediate staple guide 74 provides resistive force to the motion of staple lifter 90 and maintains the staple in contact with lifter 90 and profile 96 through motion between the staple feeding track 82a and staple forming track 120. Ears 90a on lifter 90 protrude transversely into channels 82b of lower staple housing 82 to guide motion of lifter 90. This staple transfer mechanism allows for reliable staple feeding in the staple cartridge 70 within a thin profile. This allows for improved visible staple placement onto the surgical site.

While the invention has been described in connection with a particularly preferred embodiment, it will be understood that the following claims and their equivalents are meant to describe the invention.

What is claimed is:

1. In a surgical stapler having a plurality of staples and an anvil placed distally from said staples and a staple former proximally displaced from said anvil, which shapes said staples about said anvil, said staples having a pair of sharpened legs connected by a crown and said legs in an unformed staple extending angularly from said crown in a proximal direction, said former having a rectangular inner profile and edges for contacting said legs, the improvement comprising said edges having an angular profile extending from said inner profile in a proximal direction such that when said staple crown contacts said anvil, said angular profile contacts said staple legs so that said former is able to form said staple legs about said anvil.

2. In the stapler of claim 1, said staple legs bending around said crown along the said edges of said former and said anvil, the improvement further comprising said former configured so that said edges contact said staple legs before said inner profile begins to bend said legs.

3. The stapler of claim 2 wherein said anvil is shorter than an unformed crown of one of said staples.

* * * * *